United States Patent
Aburdeineh et al.

(10) Patent No.: US 8,337,915 B2
(45) Date of Patent: *Dec. 25, 2012

(54) FENUGREEK SEED EXTRACT TO LOWER BLOOD CHOLESTEROL

(76) Inventors: S George Aburdeineh, Falls Church, VA (US); Hikmat George Aburdeineh, Bethlehem (IL)

(*) Notice: Subject to any disclaimer, the term of this patent is extended or adjusted under 35 U.S.C. 154(b) by 872 days.

This patent is subject to a terminal disclaimer.

(21) Appl. No.: 11/030,886

(22) Filed: Jan. 10, 2005

(65) Prior Publication Data

US 2005/0153001 A1   Jul. 14, 2005

Related U.S. Application Data

(60) Provisional application No. 60/535,731, filed on Jan. 10, 2004.

(51) Int. Cl.
*A61K 131/00* (2006.01)
*A61K 36/48* (2006.01)
*A61P 43/00* (2006.01)
*A61P 3/06* (2006.01)

(52) U.S. Cl. .................. 424/757; 424/776; 514/7.4

(58) Field of Classification Search .................. None
See application file for complete search history.

(56) References Cited

U.S. PATENT DOCUMENTS

| | | | |
|---|---|---|---|
| 4,834,990 A | | 5/1989 | Amer |
| 5,009,819 A | | 4/1991 | Popescu et al. |
| 5,368,870 A | * | 11/1994 | Efstathiou |
| 5,558,897 A | | 9/1996 | Goldman |
| 5,851,578 A | | 12/1998 | Gandhi |
| 6,565,896 B1 | * | 5/2003 | Gorsek |

FOREIGN PATENT DOCUMENTS

IN   189720 A1 *  4/2003

OTHER PUBLICATIONS

Nada, SA et al. Fitoterpia, 1997. 68(3): 240-244. Evaluatio of the hypoglycemic activity of a traditional herbal preparation in male diabetic rats.*
Green, J. The Herbal Medicine-Maker's Handbook: A Home Manual, 2000. The Crossing Press, U.S.A. Chapter 9: Decoction, pp. 112-115.*
Bensky, D et al. Chinese Herbal Medicine: Formulas & Strategies, 1990. Eastland Press, Inc., USA, pp. 16-23.*
Al-Hussary, Naj. Iraqi Journal of Veterinary Sciences (1993): 6(2): 102-105. Effect of fenugreek seeds decoction on blood glucose, cholesterol and triglycerides levels in normal and alloxan diabetic rats.*
Wang, H. X., et al. Life Sciences, (65): 2663-2677 (1990). Natural products with hypoglycemic, hypotensive, hypocholesterolemic, antiatherosclerotic and antithrombotic activities.*

* cited by examiner

*Primary Examiner* — Michele Flood
(74) *Attorney, Agent, or Firm* — DLA Piper LLP (US)

(57) ABSTRACT

A method of lowering blood cholesterol in a non-diabetic patient by at least 30% is described. The method involves orally administering for 30 consecutive days a fenugreek seed extract composition. Various methods of preparation and various formulations are described. Physiologically effective pharmaceutical compositions and beverages containing fenugreek seed extracts and other active components are also disclosed.

10 Claims, No Drawings

FENUGREEK SEED EXTRACT TO LOWER BLOOD CHOLESTEROL

CROSS-REFERENCE TO RELATED APPLICATIONS

This application claims benefit under 35 U.S.C. §119(e) of U.S. provisional patent application No. 60/535,731, filed Jan. 10, 2004, the disclosure of which is herein incorporated by reference.

BACKGROUND OF THE INVENTION

The present invention is directed to relatively stable, convenient and patient-friendly compositions of fenugreek seed extract, including pharmaceutically acceptable compositions thereof. The invention further provides a method for preparing such compositions. The compositions of this invention are advantageously used in methods for treating a non-diabetic individual having a disorder associated with high cholesterol. Specifically, the present invention includes employing fenugreek seed extract, or compositions or formulations comprising them, to lower cholesterol in a non-diabetic to a greater degree compared to conventional preparations. Fenugreek seed extracts, or compositions or formulations comprising them, have several advantages, including: the capability of daily oral dosing, ease of use in suspension form, safety, efficacy, purity, relative stability, and resuspendability over a short period of time.

The invention relates to an extraction process that uses fenugreek, fenugreek extracts or grinds (herein referred to as "juice" or "extract"). The instant compositions also encompass carbonated or non-carbonated beverages and formulations containing the aforementioned fenugreek extract which may further contain minerals, vitamins, nutrients, standard excipients, carriers, physiologically active agents, etc. The formulation may be in a ready-to-drink form in a container, a concentrate, or as a powder mix to be reconstituted with water or other ingestible liquids. Moreover, it may be compounded in the form of a pill, capsule, granules, microparticles, nanoparticles or liposomes.

The instant inventors have discovered that treating non-diabetic patients suffering from high cholesterol levels with the above-mentioned composition(s) significantly lowers the patient's cholesterol levels. While it may be anticipated that any soluble fiber may achieve a decrease in the blood cholesterol level (U.S. Pat. Nos. 4,834,990, 5,009,819, 5,558,897 and 5,851,578, incorporated herein by reference), the instant process yields the following unexpected result. While the prior art generally discloses a reduction of several points using "juices" such as those of fenugreek often in the range of 5-15 points (which is in the general range of 2-10%), the inventors compositions(s) derived via the specific extraction process yields invariably reductions in the range of 30% or higher (Table 1). For instance, consuming little amounts of fenugreek "juice" over thirty days of consecutive usage provides dramatic results enumerated herein. This data is unprecedented in the literature. In fact, such a result is neither disclosed in the prior art nor would it be obvious to one of ordinary skill in the art.

As stated above, the present invention also provides a ready-to-drink beverage or a concentrate in a solid (e.g., powder mix) or a liquid form for reconstitution into a beverage. Furthermore, such beverages may be supplemented with soluble minerals (e.g., calcium), vitamins, soluble fibers, flavors, colors, adjuvants, taste-masking agents, conventional solvents and carriers.

Commercially marketed fiber-containing products are not often well received by patients with respect to taste and appearance of the final product at the time of consumption. The present invention alleviates these problems.

The present invention also has the advantage of simplicity of extraction. The present inventors have discovered that simply boiling fenugreek seeds in water results in an extraction (the "juice" or "extract") that can be directly employed in the claimed compositions to lower cholesterol to the specified degree.

Furthermore, the instant inventors have also noted the following benefits of using fenugreek "juice" (without any observed side effects):
1) alleviation of a woman's birth pains;
2) aiding women suffering from a lack of estrogen;
3) regulating menstrual period;
4) assisting in milk production in nursing women;
5) treating rheumatism;
6) treating cough and sore throat pain; and
7) acting as a sexual stimulant in women.

TABLE 1

| Case # | Age | Sex | Cholesterol levels prior to fenugreek treatment (mg/100 ml) | Cholesterol levels following one month of fenugreek treatment (mg/100 ml) | % Decrease | Cholesterol levels following three months of fenugreek treatment (mg/100 ml) | % Decrease | Cholesterol levels following one year of fenugreek treatment (mg/100 ml) | % Decrease |
|---|---|---|---|---|---|---|---|---|---|
| 1 | 33 | M | 320 | 280 | 12.5 | 240 | 25 | 190 | 40.6 |
| 2 | 41 | M | 280 | 220 | 21.4 | 180 | 35.7 | 150 | 46.4 |
| 3 | 48 | M | 330 | 280 | 15 | 240 | 27 | 180 | 45.5 |
| 4 | 57 | M | 285 | 255 | 10.5 | 215 | 24.6 | 205 | 28.1 |
| 5 | 52 | M | 337 | 245 | 27.3 | 200 | 40.7 | 165 | 51 |
| 6 | 44 | M | 295 | 265 | 10.2 | 215 | 27.1 | 198 | 33 |
| 7 | 48 | M | 305 | 285 | 7 | 255 | 16.4 | 204 | 33.1 |
| 8 | 39 | M | 440 | 380 | 13.6 | 285 | 35.2 | 205 | 53.4 |
| 9 | 65 | M | 276 | 245 | 11.2 | 205 | 25.7 | 155 | 43.8 |
| 10 | 58 | M | 288 | 238 | 17.4 | 220 | 23.6 | 210 | 27.1 |
| 11 | 48 | M | 305 | 245 | 19.7 | 185 | 39.3 | 175 | 42.6 |
| 12 | 47 | M | 265 | 245 | 7.5 | 235 | 11.3 | 215 | 18.9 |
| 13 | 55 | M | 276 | 266 | 3.6 | 260 | 5.8 | 235 | 14.9 |
| 14 | 62 | M | 457 | 352 | 23 | 320 | 30 | 265 | 42 |
| 15 | 27 | M | 305 | 265 | 13.1 | 255 | 16.4 | 210 | 31.1 |
| 16 | 55 | M | 330 | 290 | 12.1 | 260 | 21.1 | 199 | 39.7 |

TABLE 1-continued

| Case # | Age | Sex | Cholesterol levels prior to fenugreek treatment (mg/100 ml) | Cholesterol levels following one month of fenugreek treatment (mg/100 ml) | % Decrease | Cholesterol levels following three months of fenugreek treatment (mg/100 ml) | % Decrease | Cholesterol levels following one year of fenugreek treatment (mg/100 ml) | % Decrease |
|---|---|---|---|---|---|---|---|---|---|
| 17 | 25 | M | 345 | 245 | 29 | 235 | 32 | 225 | 35 |
| 18 | 36 | M | 294 | 230 | 22 | 210 | 29 | 189 | 36 |
| 19 | 47 | M | 282 | 252 | 11 | 222 | 21.3 | 185 | 34.4 |
| 20 | 32 | M | 288 | 232 | 19.4 | 210 | 27.1 | 155 | 46.2 |
| 21 | 53 | M | 270 | 235 | 13 | 215 | 20.4 | 195 | 28 |
| 22 | 60 | M | 284 | 235 | 17.3 | 185 | 35 | 175 | 38.4 |
| 23 | 61 | M | 295 | 245 | 17 | 215 | 27.1 | 200 | 32.2 |
| 24 | 33 | M | 340 | 240 | 29.4 | 200 | 41.2 | 192 | 44 |
| 25 | 22 | M | 290 | 210 | 27.6 | 190 | 34.5 | 182 | 37.2 |
| 26 | 42 | M | 287 | 255 | 11.1 | 220 | 23.3 | 185 | 35.5 |
| 27 | 60 | M | 290 | 265 | 8.6 | 240 | 17.2 | 185 | 36.2 |
| 28 | 58 | M | 280 | 270 | 3.6 | 230 | 17.9 | 220 | 21.4 |
| 29 | 40 | M | 275 | 245 | 10.9 | 220 | 20 | 185 | 32.7 |
| 30 | 32 | M | 455 | 380 | 16.5 | 290 | 36.3 | 220 | 51.6 |
| 31 | 45 | M | 295 | 220 | 25.4 | 190 | 35.6 | 170 | 42.4 |
| 32 | 43 | M | 270 | 245 | 9.3 | 210 | 22.2 | 200 | 26 |
| 33 | 24 | M | 290 | 265 | 8.6 | 210 | 27.6 | 195 | 32.8 |
| 34 | 47 | M | 290 | 245 | 15.5 | 205 | 29.3 | 175 | 39.7 |
| 35 | 45 | M | 297 | 265 | 10.8 | 220 | 26 | 200 | 32.7 |
| 36 | 51 | M | 330 | 285 | 13.6 | 245 | 25.8 | 199 | 40 |
| 37 | 47 | M | 280 | 210 | 25 | 200 | 28.6 | 185 | 40 |
| 38 | 78 | M | 295 | 235 | 20.3 | 215 | 27.1 | 193 | 34.6 |
| 39 | 41 | M | 260 | 210 | 19.2 | 200 | 23.1 | 185 | 29 |
| 40 | 29 | M | 299 | 236 | 21.1 | 205 | 31.5 | 198 | 33.8 |
| 41 | 16 | M | 335 | 285 | 19.8 | 220 | 38 | 195 | 45.1 |
| 42 | 46 | M | 298 | 256 | 14.1 | 225 | 24.5 | 205 | 31.2 |
| 43 | 24 | M | 270 | 225 | 16.7 | 205 | 24 | 200 | 26 |
| 44 | 45 | M | 260 | 215 | 17.3 | 195 | 25 | 180 | 30.8 |
| 45 | 41 | M | 250 | 210 | 16 | 200 | 20 | 190 | 24 |
| 46 | 55 | M | 270 | 245 | 9.3 | 215 | 20.4 | 195 | 27.8 |
| 47 | 28 | M | 280 | 250 | 10.7 | 210 | 25 | 200 | 28.6 |
| 48 | 22 | M | 310 | 290 | 6.5 | 245 | 20.9 | 198 | 36.1 |
| 49 | 35 | M | 295 | 290 | 0 | 310 | 0 | 295 | 0 |
| 50 | 48 | M | 345 | 355 | 0 | 340 | 0 | 348 | 0 |
| 51 | 55 | M | 295 | 298 | 0 | 290 | 0 | 310 | 0 |
| 52 | 45 | M | 280 | 280 | 0 | 275 | 0 | 285 | 0 |
| 53 | 38 | F | 390 | 320 | 18 | 260 | 33.3 | 230 | 41 |
| 54 | 41 | F | 355 | 280 | 21.1 | 220 | 38 | 185 | 47.9 |
| 55 | 42 | F | 450 | 350 | 22.2 | 320 | 28.9 | 230 | 48.9 |
| 56 | 47 | F | 290 | 270 | 6.9 | 220 | 24.1 | 175 | 39.7 |
| 57 | 55 | F | 425 | 375 | 11.8 | 325 | 23.5 | 240 | 43.5 |
| 58 | 45 | F | 335 | 285 | 14.9 | 265 | 20.9 | 185 | 44.8 |
| 59 | 43 | F | 296 | 221 | 25.3 | 185 | 37.5 | 155 | 47.6 |
| 60 | 35 | F | 270 | 245 | 9.2 | 205 | 24.1 | 145 | 46.3 |
| 61 | 32 | F | 265 | 205 | 22.7 | 165 | 37.7 | 110 | 58.5 |
| 62 | 31 | F | 260 | 195 | 25 | 175 | 32.7 | 135 | 48.1 |
| 63 | 37 | F | 245 | 195 | 20.4 | 155 | 36.7 | 125 | 49 |
| 64 | 35 | F | 280 | 240 | 14.3 | 192 | 31.4 | 180 | 35.7 |
| 65 | 49 | F | 285 | 220 | 22.8 | 210 | 26.3 | 205 | 28.1 |
| 66 | 56 | F | 295 | 215 | 27.1 | 205 | 30.5 | 185 | 37.3 |
| 67 | 41 | F | 268 | 210 | 21.6 | 196 | 26.9 | 145 | 45.9 |
| 68 | 46 | F | 295 | 255 | 13.6 | 195 | 33.9 | 190 | 35.6 |
| 69 | 59 | F | 278 | 244 | 12.2 | 215 | 22.7 | 202 | 27.3 |
| 70 | 55 | F | 245 | 185 | 24.5 | 155 | 36.7 | 135 | 44.9 |
| 71 | 50 | F | 560 | 495 | 11.6 | 432 | 22.9 | 298 | 46.8 |
| 72 | 66 | F | 332 | 285 | 14.2 | 234 | 29.5 | 200 | 39.8 |
| 73 | 44 | F | 260 | 220 | 15.4 | 195 | 25 | 165 | 36.5 |
| 74 | 59 | F | 290 | 240 | 17.2 | 195 | 32.8 | 165 | 43.1 |
| 75 | 37 | F | 305 | 205 | 32.8 | 175 | 42.6 | 155 | 49.2 |
| 76 | 69 | F | 295 | 265 | 10.2 | 210 | 28.8 | 200 | 32.2 |
| 77 | 55 | F | 275 | 255 | 7.3 | 215 | 21.8 | 195 | 29.1 |
| 78 | 24 | F | 290 | 230 | 20.7 | 198 | 31.7 | 170 | 41.4 |
| 79 | 47 | F | 310 | 265 | 14.5 | 245 | 21 | 200 | 35.5 |
| 80 | 48 | F | 270 | 210 | 22.2 | 190 | 29.6 | 180 | 33.3 |
| 81 | 38 | F | 310 | 255 | 17.7 | 220 | 29 | 185 | 40.3 |
| 82 | 57 | F | 277 | 210 | 24.2 | 185 | 33.2 | 155 | 44 |
| 82 | 33 | F | 288 | 245 | 14.9 | 198 | 31.3 | 185 | 35.8 |
| 84 | 68 | F | 280 | 200 | 28.6 | 192 | 31.4 | 165 | 41.1 |
| 85 | 44 | F | 285 | 255 | 10.5 | 210 | 26.3 | 195 | 31.6 |
| 86 | 37 | F | 275 | 225 | 18.2 | 205 | 25.5 | 173 | 37.1 |
| 87 | 82 | F | 310 | 255 | 17.7 | 225 | 27.4 | 196 | 36.8 |
| 88 | 75 | F | 286 | 255 | 10.8 | 210 | 26.6 | 200 | 30.1 |

TABLE 1-continued

| Case # | Age | Sex | Cholesterol levels prior to fenugreek treatment (mg/100 ml) | Cholesterol levels following one month of fenugreek treatment (mg/100 ml) | % Decrease | Cholesterol levels following three months of fenugreek treatment (mg/100 ml) | % Decrease | Cholesterol levels following one year of fenugreek treatment (mg/100 ml) | % Decrease |
|---|---|---|---|---|---|---|---|---|---|
| 89 | 53 | F | 265 | 210 | 20.8 | 195 | 26.4 | 190 | 28.3 |
| 90 | 42 | F | 280 | 255 | 8.9 | 220 | 21.4 | 200 | 28.6 |
| 91 | 47 | F | 291 | 240 | 17.5 | 210 | 27.8 | 195 | 33 |
| 92 | 77 | F | 295 | 265 | 10.2 | 225 | 23.7 | 195 | 33.9 |
| 93 | 44 | F | 288 | 265 | 8 | 235 | 18.4 | 215 | 25.3 |
| 94 | 48 | F | 350 | 285 | 18.6 | 235 | 32.9 | 200 | 42.9 |
| 95 | 52 | F | 285 | 235 | 17.5 | 200 | 29.8 | 175 | 38.6 |
| 96 | 39 | F | 275 | 245 | 10.9 | 215 | 21.8 | 200 | 27.3 |
| 97 | 57 | F | 265 | 210 | 20.8 | 200 | 24.5 | 180 | 30.1 |
| 98 | 28 | F | 285 | 285 | 0 | 275 | 0 | 290 | 0 |
| 99 | 62 | F | 315 | 310 | 0 | 320 | 0 | 305 | 0 |

DETAILED DESCRIPTION OF THE INVENTION

Unless otherwise defined herein, scientific and technical terms used in connection with the present invention shall have the meanings that are commonly understood by those of ordinary skill in the art. Furthermore, unless otherwise required by context, singular terms shall include pluralities and plural terms shall include the singular. Generally, nomenclatures used in connection with, and standard techniques described herein are those well known and commonly used in the art.

For millennia, fenugreek (Trigonella foenum graecum) has been used both as a medicine and as a food spice in India and the Middle East. Fenugreek seeds have been used for centuries by practitioners of Indian Ayurvedic medicine as well as traditional Chinese Medicine. The fenugreek plant is native to the Mediterranean areas of Europe and to India. Fenugreek is generally regarded as safe and non-toxic. In India its leaves are cooked as a vegetable and also used as animal feed. Fresh seeds are often used as flavoring or sprouted and eaten as a salad green. Fenugreek seeds have a slight maple taste and are often used in production of imitation maple flavorings. The fenugreek plant produces small white flowers in late summer and after the flowers die, large pods that contain 10-20 irregularly-shaped yellow seeds develop. In some parts of the world, dried fenugreek seeds are ground for a curry spice. However, they may also be boiled to produce a yellow dye, roasted as a coffee substitute, or used to flavor foods and tobacco. After the seeds are collected from the plants, the plants may be chopped and used as fertilizer.

Recent interest in fenugreek focuses on its potential benefits to lower blood sugar in diabetics. In some individuals dietary intake of soluble fiber can slow absorption and subsequent digestion of food that results in a slower rise in blood sugar levels. Some clinical studies have demonstrated that fenugreek seeds reduce blood glucose levels and decrease insulin resistance in mild type-2 diabetic patients. Fenugreek contains the amino acid, 4-hydroxyisoleucine, which appears to increase the body's production of insulin when blood sugar levels are elevated.

Studies have also shown that fenugreek may lower levels of triglycerides and serum cholesterol levels in diabetics. In terms of weight control, the soluble fiber in fenugreek seeds can reduce dietary fat absorption by binding to fatty acids as well as create a sensation of "fullness," thereby reducing appetite. Finally, because fenugreek seeds contain estrogen-like saponins, blood levels of total cholesterol, LDL and triglycerides can be reduced (with no change in HDL). Although it is by no means the only major risk factor, elevated serum cholesterol is associated with a greater risk of heart disease. Cholesterol levels under 200 mg/dl are considered optimal. However a low cholesterol level is not any guarantee of good heart health, since some people with low cholesterol levels do suffer heart attacks. Evaluation of changes in cholesterol requires consultation with a healthcare professional and should include measurement of total serum cholesterol, as well as HDL and LDL cholesterol. The present inventors observed no side effects or poisoning as a result of consuming the fenugreek "juice," even in large quantities. In fact, it was observed that doping or consuming mega-dose has no effect versus dosing in light quantity. The inventors found that amounts as little as two ounces per day for 30 days provided the therapeutic effect. Other patients consumed as much as about five cups a day to derive the identical beneficial effect.

Fenugreek seed extracts may also have other medical uses. It may reduce the amounts of calcium oxalate in the kidneys, often a contributing factor in kidney stones. In animal studies, fenugreek also appeared to lessen the chance of developing colon cancer by blocking the action of certain enzymes. Topically, the gelatinous texture of fenugreek seed may have some benefit for soothing skin that is irritated by eczema or other conditions. It has also been applied as a warm poultice to relieve muscle aches and gout pain. To be applied topically, fenugreek seeds can be ground into a powder, and then soaked in hot water to form a thick gel. Fenugreek is a mild but effective laxative.

The instant fenugreek extract or "juice" can be combined with any pharmaceutically acceptable excipient. According to this invention, a "pharmaceutically acceptable excipient" is an excipient that acts as filler or a combination of fillers used in pharmaceutical compositions. Preferred excipients included in this category are: 1) amino acids, such as glycine, arginine, aspartic acid, glutamic acid, lysine, asparagine, glutamine, proline; 2) carbohydrates, e.g., monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-β-cyclodextrin and alike; 8) inorganic molecules, such as sodium chloride, potassium chloride, magnesium chloride, phosphates of sodium and potassium, boric acid, ammonium carbonate and ammonium phosphate; 9) organic molecules, such as acetates, citrate, ascorbate, lactate; 10) emulsifying or solubilizing/stabilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol. Salts of such compounds may also be used. A further preferred group of excipients includes sucrose, trehalose, lactose, sorbitol, lactitol, mannitol, inositol, salts of sodium and potassium, such as acetate, phosphates, citrates and borate, glycine, arginine, polyethylene oxide, polyvinyl alcohol, polyethylene glycol, hexylene glycol, methoxy polyethylene glycol, gelatin, hydroxypropyl-β-cyclodextrin, polylysine and polyarginine.

The fenugreek extract or "juice" according to this invention can also be combined with a carrier or excipient, a substance that, when added to a therapeutic, speeds or improves its action. Examples of carriers or excipients include, for example, buffer substances, such as phosphates, glycine, sorbic acid, potassium sorbate, partial glyceride mixtures of saturated vegetable fatty acids, waters, salts or electrolytes, such as Protamine sulfate, disodium hydrogen phosphate, sodium chloride, zinc slats, colloidal silica, magnesium, trisilicate, cellulose-based substances and polyethylene glycol.

This invention advantageously permits consumption of the instant fenugreek extract or "juice" by a human. In one embodiment, the compositions according to this invention are administered about once a day. In another embodiment, the compositions according to this invention are administered about once a day for a month. In yet another embodiment, the compositions according to this invention are administered for a period longer than a month. It will be appreciated by those of skill in the art that the specific treatment regimen will depend upon factors such as the cholesterol level in the patient, the age and weight of the patient to be treated, general physical condition of the patient and the judgment of the treating physician.

In order that this invention may be better understood, the following examples are set forth. These examples are for the purpose of illustration only and are not to be construed as limiting the scope of the invention in any manner. Numerous other variations of the present invention will be appreciated by those skilled in the art, in view of the disclosure herein. The exact compositions, methods of preparation and embodiments shown are not limiting of the invention, and any obvious modifications will be apparent to one skilled in the art.

EXAMPLE 1

Extraction may be carried out in one of the following three ways:

Simple Extraction: Soak about ⅓ cup of fenugreek seeds in about 15 cups of water for 8-10 hours. Bring the mixture to a boil for about 5-7 minutes. Cool, strain and refrigerate the extracted "juice."

Quick Extraction: Combine about ⅓ cup fenugreek seeds in about 15 cups of water and bring to a boil for about 10 minutes. Cool, strain and refrigerate the extracted "juice."

Preferred Extraction: Grind about ⅓ cup of fenugreek seed to a powder. Combine the resulting powder with about 15 cups of water and bring to a boil for 10 minutes. Cool, strain and refrigerate the extracted "juice."

Note: The noted boiling times above are only preferred embodiments and may be considerably shorter or longer. Similarly, the proportion of seed to water employed may be scaled appropriately. The simple extraction method described above produces a slightly more opaque product. The best way to store fenugreek is to keep the seed in a cool and dry place. This allows for it to be kept for several months without loss in activity. Once the seed is ground or powdered, it does not keep well and must be used promptly. As soon as the "juice" is extracted, whether from the seed or the grind, it is preferred that it be kept refrigerated.

EXAMPLE 2

Reconstitution of the extracted "Juice" may be accomplished by the following method:

As stated earlier, while the exact composition of the final beverage may be in the form of the extracted "juice," tea or carbonated beverage, a small quantity taken each day for 30 consecutive days provides a reduction in blood cholesterol of 30% or more. An individual serving of tea may be prepared by boiling a teaspoon of fresh powdered/ground fenugreek seed in a cup of water for ten minutes. Appropriate flavors, conventional carriers, excipients or additives may be additionally incorporated into the extracted "juice." Examples include sweeteners (e.g., honey, sugar, aspartame, etc.) or flavors (e.g., lemon, anise, mint, etc.). Additionally, these beverages may be supplemented with various nutrients, vitamins, minerals, pharmaceutically active agents, fibers, liposomes and herbal extracts.

It is understood that the invention is not limited to the disclosed compositions, methods of preparation and embodiments shown, including any embodiments that may be apparent to one of ordinary skill in the art. Although the foregoing invention has been described in some detail by way of illustration and examples for purposes of clarity of understanding, it will be readily apparent to those of ordinary skill in the art in light of the teachings of this invention that certain variations and modifications may be made thereto without departing from the spirit or scope of the disclosure herein, including the specific embodiments.

We claim:

1. A method of lowering blood cholesterol in a non-diabetic human by at least 30% comprising orally administering for at least 30 days to a non-diabetic human in need thereof an effective amount of a composition consisting essentially of a fenugreek (*Trigonella foenum graecum*) seed extract; and, optionally an agent selected from the group consisting of a pharmaceutically acceptable excipient, lubricant, binder, glidant, filler, flavoring agent, masking agent, vitamin, mineral, a carrier and mixtures thereof.

2. A method of lowering blood cholesterol in a non-diabetic human by at least 30% comprising orally administering for at least 30 days to a non-diabetic human in need thereof an effective amount of a composition consisting essentially of a fenugreek (*Trigonella foenum graecum*) seed extract; and, optionally an agent selected from the group consisting of a pharmaceutically acceptable excipient, lubricant, binder, glidant, filler, flavoring agent, masking agent, vitamin, mineral, a carrier and mixtures thereof, wherein the administering is a dose regimen selected from the group consisting of about two ounces a day, about five cups a day, about three cups a day and about one to two cups a day.

3. The method of claim 1, wherein the composition is in the form of an oral dosage form selected from the group consisting of a pill, a capsule, granules, microparticles, nanoparticles and liposomes.

4. The method of claim 2, wherein the composition is in the form of an oral dosage form selected from the group consisting of a pill, a capsule, granules, microparticles, nanoparticles and liposomes.

5. The method of claim 1 or claim 2, further comprising administering to the subject a cholesterol lowering drug.

6. The method of claim 1, wherein the administering comprises orally administering an oral dosage form in the form of a liquid; and, the administering is according to a dose regimen selected from the group consisting of (a) about two ounces a day; (b) about five cups a day; (c) about three cups a day; and, (d) about one to two cups a day.

7. The method of claim 1 or claim 2, wherein the administering comprises orally administering an oral dosage form in the form of a liquid; and, the administering is according to a dose regimen selected from the group consisting of (a) about two ounces a day for 1-12 months; (b) about five cups a day for 1-12 months; (c) about three cups a day for 1-12 months; and, (d) about one to two cups a day for 1-12 months.

8. The method of claim 3 or claim 4, wherein the oral dosage form is a single dose solid enteric coated formulation.

9. The method of claim 3 or claim 4, wherein the oral dosage form is a liquid oral liposomal formulation.

10. The method of claim 3 or claim 4, wherein the oral dosage form contains a plurality of therapeutic nanoparticles.

* * * * *